United States Patent
Chen et al.

(10) Patent No.: US 11,058,733 B2
(45) Date of Patent: Jul. 13, 2021

(54) **ACTIVE SUBSTANCES OF *BIFIDOBACTERIUM LACTIS* GKK2, COMPOSITION COMPRISING THE SAME AND METHOD OF PROMOTING LONGEVITY USING THE SAME**

(71) Applicant: GRAPE KING BIO LTD, Taoyuan (TW)

(72) Inventors: Chin-Chu Chen, Taoyuan (TW); Yen-Lien Chen, Taoyuan (TW); Shih-Wei Lin, Taoyuan (TW); Yen-Po Chen, Taoyuan (TW); Ci-Sian Wang, Taoyuan (TW); Yu-Hsin Hou, Taoyuan (TW); Yang-Tzu Shih, Taoyuan (TW); Ching-Wen Lin, Taoyuan (TW); Ya-Jyun Chen, Taoyuan (TW); Jia-Lin Jiang, Taoyuan (TW)

(73) Assignee: GRAPE KING BIO LTD, Taoyuan (TW)

( * ) Notice: Subject to any disclaimer, the term of this patent is extended or adjusted under 35 U.S.C. 154(b) by 129 days.

(21) Appl. No.: 16/542,608

(22) Filed: Aug. 16, 2019

(65) Prior Publication Data
US 2020/0054692 A1 Feb. 20, 2020

(30) Foreign Application Priority Data
Aug. 16, 2018 (TW) .................................. 107128656

(51) Int. Cl.
*A61K 35/745* (2015.01)
*C12N 1/20* (2006.01)
(Continued)

(52) U.S. Cl.
CPC .......... *A61K 35/745* (2013.01); *A23L 33/135* (2016.08); *A61K 9/0056* (2013.01);
(Continued)

(58) Field of Classification Search
CPC .................................................... A61K 35/745
See application file for complete search history.

(56) References Cited

U.S. PATENT DOCUMENTS
2016/0030493 A1 2/2016 Nofar et al.

FOREIGN PATENT DOCUMENTS
CN 104839699 A 8/2015
CN 10499699 A 10/2015
(Continued)

OTHER PUBLICATIONS

Maneerat et al., "Consumption of Bifidobacterium lactis Bi-07 by healthy elderly adults enhances phagocytic activity of monocytes and granulocytes," Journal of Nutritional Science 2(e44)1-10, 2013.*
(Continued)

*Primary Examiner* — Rosanne Kosson
(74) *Attorney, Agent, or Firm* — Hayes Soloway PC

(57) ABSTRACT

The present invention provides a *Bifidobacterium lactis* having active substances, a composition comprising the same, and a method of promoting longevity using the same by subjecting the composition to a subject, thereby increasing Cisd2 gene expression, reducing damage of mitochondria, delaying aging-related symptoms including nerve degeneration and sarcopenia, and so on.

6 Claims, 12 Drawing Sheets

(51) Int. Cl.
   *A61K 9/00*       (2006.01)
   *A23L 33/135*     (2016.01)
   *A61K 35/00*      (2006.01)

(52) U.S. Cl.
   CPC ............ *A61K 9/0095* (2013.01); *C12N 1/20* (2013.01); *A23V 2002/00* (2013.01); *A23Y 2300/49* (2013.01); *A61K 2035/115* (2013.01)

(56) References Cited

FOREIGN PATENT DOCUMENTS

| | | |
|---|---|---|
| CN | 109694834 A | 4/2019 |
| JP | H034768 A | 1/1991 |
| TW | 201917205 A | 5/2019 |
| TW | 201918553 A | 5/2019 |

OTHER PUBLICATIONS

Mitsuharu Matsumoto., "Life Prolonging Effect Achieved by Using Probiotics to Control the Concentration of Polyamine in Intestine", Biological Engineering, 2013, vol. 91, Issue No. 11, pp. 632-636, 17 pages.

Tomatsu Hajime et al., "Metabolomic approach of identification of substance upregulating anti-aging polyamines production by intestinal microbiota" Medical Science Digest, 2015, vol. 41, Issue No. 4, pp. 176-180, 14 pages.

Hirotomo Ochi et al., "Retardation of senescence by Extended Intake of *Streptococcus lactis* Cell Preparation" Bifidobacteria Microflora, 1986, vol. 6, Issue No. 1, pp. 21-31, 11 pages.

"GSM Grip-Strength Meter for mice and rats"; ugo basile; 5 pages; https://www.ugobasile.com/products/catalogue/motory-coordination-grip-strength-activity/item/76-47200-grip-strength-meter-mice-and-rats.html.

"A New Murine Model of Accelerated Senescence" Takeda et al; Mechanisms of Ageing and Development, p. 183-194, 1981.

"Dose Translation from Animal to Human Studies Revisited" Reagan-Shaw et al, The FASEB Journal, pp. 659-661, Jan. 15, 2019.

"Methods to Assess Health Benefits of Health Food for Delaying Aging" Taiwan Food and Drug Administration, 2015, pp. 16-17, Section 5.1 and 5.2.

* cited by examiner

ACTIVE SUBSTANCES OF *BIFIDOBACTERIUM LACTIS* GKK2, COMPOSITION COMPRISING THE SAME AND METHOD OF PROMOTING LONGEVITY USING THE SAME

RELATED APPLICATION

This application claims priority to an earlier Taiwan Application Serial Number 107128656, filed Aug. 16, 2018, which is incorporated herein by reference in its entirety.

BACKGROUND

Field of Invention

The present invention relates to a lactic acid bacteria having active substances for promoting longevity, a composition including the same and a method of using the same. More particularly, the present invention relates to *Bifidobacterium lactis* GKK2 having active substances, a composition comprising the same and a method of promoting longevity using the same, thereby enhancing Cisd2 gene expression, decreasing mitochondrial damages and/or delaying aging-related symptoms such as neurodegenerative diseases as well as sarcopenia when subjecting to a the subject.

Description of Related Art

Longevity Gene

Scientists are eager to find the secrets of longevity. Scientists hypothesize that if a species becomes more adapted to its environment, it will be more likely to survive longer. Therefore, some scientists focus on environmental stresses such as scorching weather, or food or water deprivation, and found a group of genes that relates to stresses. In fact, these genes can function in maintaining the natural protection and repairing the activities of the biomolecules of an individual no matter how old the individual is. Additionally, these genes can enhance the survivability of the organisms, thereby enabling them to get through crises. These genes are deemed as longevity genes and can dramatically improve health and extend the lifespan of an individual as long as they are active.

Other scientists have focused on the centenarians and have evaluated the genes of these centenarians. Scientists found that compared to those with average life expectancy, the centenarians have higher expressions of some specific genes, thereby supposing that these genes are related to longer lifespans.

Cisd2 Gene

Cisd2 gene is highly conserved in the process of evolution and is found in invertebrates, vertebrates and mammals. According to this viewpoint, Cisd2 gene can control important biofunctions. The Cisd2-encoded proteins are located on the outer membrane of mitochondria. The lack of Cisd2 gene causes mitochondrial damages and affects mitochondrial structures and functions, followed by aging-related symptoms. Studies related to the Cisd2 gene show that Cisd2 knockout mice have noticeably thinner and smaller body shapes than the control group. Moreover, the mean lifespans of Cisd2 knockout mice are shorter than a half of that of the control group. In the period of experimental observation, Cisd2 knockout mice start to show symptoms such as neurodegenerative diseases and sarcopenia around the third week (equivalent to the 10 to 12 years old of a human) and have a significant weight decline around the fourth week (equivalent to the 15 years old of a human). Around the eighth week (equivalent to the 18 to 20 years old of a human), the Cisd2 knockout mice show prominent opaque eyes and osteoporosis. Around $12^{th}$ to $48^{th}$ week (equivalent to the 30 to 45 years old of a human), the Cisd2 knockout mice show progeria symptoms such as lordokyphosis, blindness, hair loss and anetoderma. Further studies on the normal aging process of wild-type mice show that the expression level of Cisd2 decreases as the mice aged, such that the expression level decreases to 60% around 14 months (equivalent to the 60 years old of a human), and decreases to 30% around 28 months (equivalent to the 90 years old of a human), respectively, when compared with young mice. Based on these findings, Cisd2 is proved to be an essential gene in regulating healthy aging and lifespan.

*Lactobacillus* spp.

*Lactobacillus* spp. exists in general environments and can convert carbohydrate into lactic acid by fermentation, thereby being applied in the manufactures of fermented foods. In the 1990s, *Lactobacillus* spp. was found to provide multiple benefits to human health and had effects on assisting digestion and improving intestinal health. Hence, people were recommended to consume more *Lactobacillus* spp. to improve the digestive environment and promote intestinal peristalsis. Moreover, since *Lactobacillus* can degrade sugar (lactose, glucose, sucrose and fructose, for example) and produce lactic acid and acetic acid to acidify intestinal environment, *Lactobacillus* spp. can inhibit the growth of bad bacteria and balance the microflora in the intestine.

Among *Lactobacillus* spp., different species of *Lactobacillus* spp. and different strains of the same species have different characteristics and different effects on the human body. For example, *L. plantarum* strains have been found to improve human health, in which *L. plantarum* PHO4 has been known to decrease blood cholesterol; *L. plantarum* 299V has been known to relieve the colitis symptoms of IL-10-deficient mice; *L. plantarum* 10hk2 has been known to increase proinflammatory mediators e.g., Interleukin (IL)-1β, IL-6 and tumor necrosis factor alpha (TNF-α) and IL-10, thereby exerting the anti-inflammatory effects, while *L. plantarum* K21 has been known to decrease blood cholesterol and triglyceride levels as well as to have anti-inflammatory effects.

*Bifidobacterium*

*Bifidobacterium* spp. are ubiquitous in the intestinal tracts, the vaginas and the oral cavity of human and animals. *Bifidobacterium* spp. are gram-positive, nonmotile, Y-shaped, and often obligate anaerobic bacteria. In 1899, *Bifidobacterium* is isolated from the fetus of healthy infants. The following studies have shown that the specific strains of *Bifidobacterium* can be applied as probiotics in the fields such as food, medicine, feed and so on.

However, no related studies have discussed the effect of lactic acid bacteria such as *Lactobacillus* and *Bifidobacterium* on the lifespan, and no experiment has proven whether the lactic acid bacteria control the lifespan of an individual by affecting the expression level of the Cisd2 gene, which evokes physiological changes and altering the lifespan of an individual.

SUMMARY

The purpose of this invention is to provide a composition comprising the *Bifidobacterium lactis* deposited in Bioresource Collection and Research Center (BCRC), Food Industry Research and Development Institute, Hsinchu 30062, Taiwan, and in China, General Microbiological Culture Collection Center (CGMCC), Institute of Microbiology Chinese Academy of Sciences, No. 1 Beichen West Road, Chaoyang District, Beijing 100101, People's Republic of China, on Jan. 12, 2018 with an accession number of BCRC 910826 and CGMCC 15205, respectively, in which the composition promotes longevity. The deposit was made under the terms of the Budapest Treaty.

Another purpose of the invention is to provide a composition including an effective dose of Bifidobacterium lactis having active substances, in which the Bifidobacterium lactis is deposited in Bioresource Collection and Research Center (BCRC), Food Industry Research and Development Institute, Hsinchu 30062, Taiwan, and in China General Microbiological Culture Collection Center (CGMCC), Chinese Academy of Sciences, Beijing 100101, People's Republic of China, on Jan. 12, 2018 with an accession number of BCRC 910826 and CGMCC 15205, respectively, and the composition promotes longevity.

Preferably, Bifidobacterium lactis having the active substances are prepared by the following steps:

(a) streaking Bifidobacterium lactis (BCRC 910826 and CGMCC 15205) onto an agar plate to produce isolated colonies; and (b) inoculating one of the isolated colonies from the step (a) in a liquid medium liquid incubation stepto obtain a liquid culture.

Preferably, the Bifidobacterium lactis having the active substances are further prepared by following steps:

(c) centrifuging the liquid culture from the step (b) to obtain a pellet; and (d) performing a lypholization on the pellet from the step (c) to obtain the Bifidobacterium lactis (BCRC 910826, and also CGMCC 15205) having the active substances.

Preferably, a temperature is set from 35 to 50° C., with ventilation from zero to 1 vvm of N2 or CO2, at a rotational speed from 10 to 100 rpm in an incubation period from 16 to 24 hours.

Preferably, a temperature for the lypholization in the step (d) is set from −196 to −40° C.

Preferably, the composition can include an additive or a combination selected from the group consisting of an excipient, a preservative, a diluent, a filler, an absorbefacient, a sweetener and/or a combination thereof.

Preferably, the composition can be a drug, a feed, a drink, a nutritional supplement, a dairy product, a geriatric food, a baby food, a non-staple food or health food.

Preferably, the form of composition can be is powder, a tablet, a pellet, a suppository, a microcapsule, an ampoule, a liquid or a spray.

The other purpose of the invention is to provide A method of promoting longevity by subjecting a composition comprising Bifidobacterium lactis (CGMCC 15205) having active substances to a subject.

Preferably, the composition enhances gene expression of Cisd2 of the subject.

Preferably, the composition decreases and/or delays mitochondrial damage of the subject.

Preferably, the composition decreases and/or delays aging-related symptoms including neurodegenerative diseases, sarcopenia, or the combination thereof of the subject.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
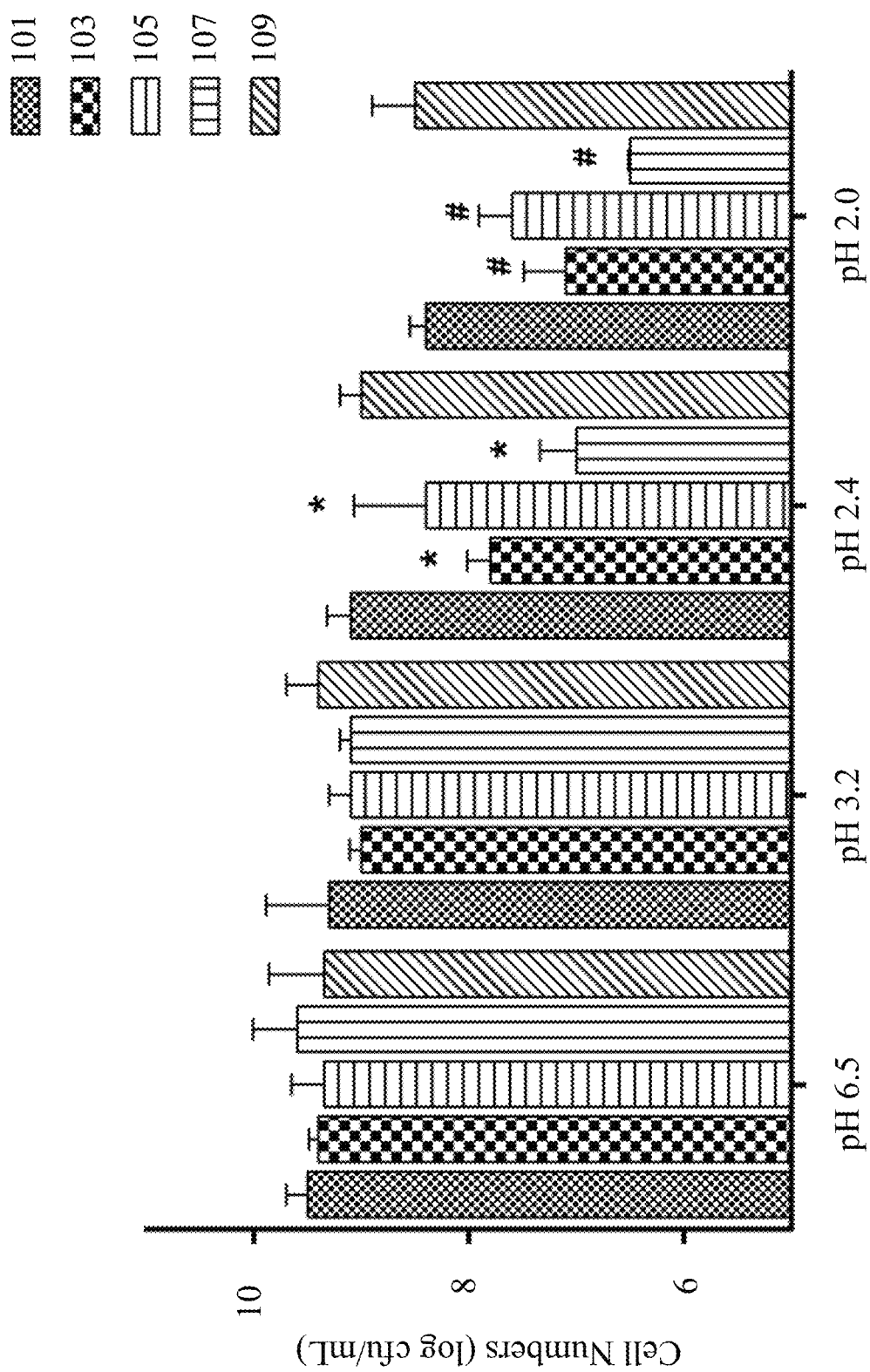
FIG. 1 shows the cell numbers of the acid tolerance test.

Reference will now be made in details to the present embodiments of the invention, examples of which are illustrated in the accompanying drawings. Wherever possible, the same reference numbers used in the drawings and the description are referred to the same or like parts.

Origin of Strains

Lactic acid bacteria used in the experiment included Lactobacillus spp. and Bifidobacterium spp. In one preferred embodiment, the lactic acid bacteria strains were purchased from Bioresource Collection and Research Center (BCRC) of Food Industry Research and Development Institute (FIRDI) at No. 331 on Shih-Pin Road, Hsinchu, Taiwan. In one preferred embodiment, the number (NO.), the species, and the accession numbers of the lactic acid bacteria strains NOs. A to J used in following experiments were listed in Table 1. Taiwan patent application NO. 106137773 and NO. 106136134 showed further information of collections, processes of isolation and purification as well as gene analyses and results of identification of the strains.

TABLE 1

Number, Species and Depository Accession Number of Lactic Acid Bacteria Strains:

| NO. | Species | Depository accession number | |
|-----|---------|----------------------------|---|
| A | Lactobacillus paracasei GKS6 | BCRC 910788 | CGMCC 14566 |
| B | Lactobacillus johnsonii | BCRC 19194 | ATCC 33200 |
| C | Lactobacillus brevis | BCRC 12187 | ATCC 14869 |
| D | Lactobacillus plantarum | BCRC 80061 | ATCC 14917 |
| E | Lactobacillus plantarum | BCRC 80581 | CICC 20764 |
| F | Lactobacillus plantarum | BCRC 80577 | NCIMB 700704 |
| G | Lactobacillus plantarum | BCRC 80578 | NCIMB 70072 |
| H | Lactobacillus plantarum GKM3 | BCRC 910787 | CGMCC 14565 |

TABLE 1-continued

Number, Species and Depository Accession Number of Lactic Acid Bacteria Strains:

| NO. | Species | Depository accession number | |
|---|---|---|---|
| I | *Bifidobacterium lactis* GKK2 | BCRC 910826 | CGMCC 15205 |
| J | *Bifidobacterium lactis* | BCRC 17394 | DCM 101040 |

BCRC: Bioresource Collection and Research Center of Food Industry Research and Development Institute (FIRDI) at No. 331 on Shih-Pin Road, Hsinchu, Taiwan.
CGMCC: China General Microbiological Culture Collection Center, Chinese Academy of Sciences, Beijing 100101, People's Republic of China.
ATCC: American Type Culture Collection, Virginia VA 20110, USA.
CICC: China Center of Industrial Culture Collection, China National Research Institute Of Food & Fermentation Industries (CNIF), Beijing 100000, People's Republic of China.
NCIMB: National Collection of Industrial Food and Marine Bacteria, Scotland's Rural College (SRUC), Aberdeen AB21 9YA, UK.
DCM: DSM 15954 in Leibniz-Institut DSMZ-Deutsche Sammlung von Mikroorganismen und Zellkulturen GmbH, Braunschweig 38124, German.

Phenotypic Analysis

A phenotypic analysis was a study comparing phenotypic differences between the lactic acid bacteria strain NO. I and other strains by an acid tolerance test, a bile tolerance test and a heat tolerance test.

Acid Tolerance Test

A total of five strains, GKK2, BCRC 17394 purchased from BCRC, *B. animalis* subsp. *Lactis* Bi 04 (Bi 04, deposited with an accession number of ATCC SD 5219 in American Type Culture Collection, ATCC), *B. animalis* subsp. *Lactis* BB-12 (BB-12, deposited with an accession number of DSM 15954 in Leibniz-Institut DSMZ-Deutsche Sammlung von Mikroorganismen and Zellkulturen GmbH), and *B. animalis* subsp. *Lactis* Bi 07 (Bi 07, deposited with an accession number of ATCC SD 5220 in ATCC) were recovered. The original De Man, Rogosa and Sharpe (MRS) liquid medium with a pH value about 6.5 was then adjusted with HCl to three different pH values: about pH 3.2, pH 2.4 and pH 2.0. The strains were inoculated in the aforementioned MRS liquid media, followed by serial dilution, spread plate, incubation and finally colony count.

FIG. 1 represented the result of acid tolerance test. The horizontal axis represented the pH values of different medium, and the vertical axis showed the cell numbers as log colony-forming units per milliliter (cfu)/mL. The bars 101, 103, 105, 107, 109 represented the lactic acid bacteria strains GKK2, BCRC 17394, DSM 15954 (BB-12), ATCC SD 5220 (Bi 07) and ATCC SD 5219 (Bi 04), respectively. The symbols "*" and "#" represented a significant difference between GKK2 and the other lactic acid bacteria strains at the same pH value (p<0.05).

As shown in FIG. 1, the cell number of the strain GKK2 (bar 101) and that of the other four strains (bar 103, 105, 107 and 109) reached to $5 \times 10^9$ cfu/mL when they were cultured in the original pH value (about pH 6.5). When the pH values of the MRS liquid medium decreased to pH 3.2, the cell numbers of all strains slightly declined, and there was no statistically significant difference in the cell numbers between the strain GKK2 and the four other strains. When the pH values of the MRS liquid medium decreased to pH 2.4 or 2.0, the cell numbers of BCRC 17394 (bar 103), BB-12 (bar 105) and Bi07 (bar 107) decreased from $10^6$ to $10^7$ cfu/mL. These numbers were significantly lower than that of GKK2, which remained its cell number to be more than $10^8$ cfu/mL (p<0.05). Accordingly, the viable cell number of the strain GKK2 was significantly higher than that of other strains in an acid environment. The results of the experiment indicated that compared to other strains, GKK2 had a better acid resistance, and thus GKK2 had a better gastric acid resistance when passing through a stomach.

Bile Tolerance Test

A total of five strains, GKK2, BCRC 17394 purchased from BCRC, *B. animalis* subsp. *Lactis* Bi 04 (deposited with an accession number of ATCC SD 5219 in ATCC), *B. animalis* subsp. *Lactis* BB-12 (deposited with an accession number of DSM 15954 in Leibniz-Institut DSMZ-Deutsche Sammlung von Mikroorganismen and Zellkulturen GmbH), and *B. animalis* subsp. *Lactis* Bi 07 (deposited with an accession number of ATCC SD 5220 in ATCC) were recovered. The strains were inoculated in the aforementioned MRS liquid medium with 0.3% bile salt and incubated at 37° C. for half an hour, followed by serial dilution, spread plate, incubation and finally colony count.

Figure 2:
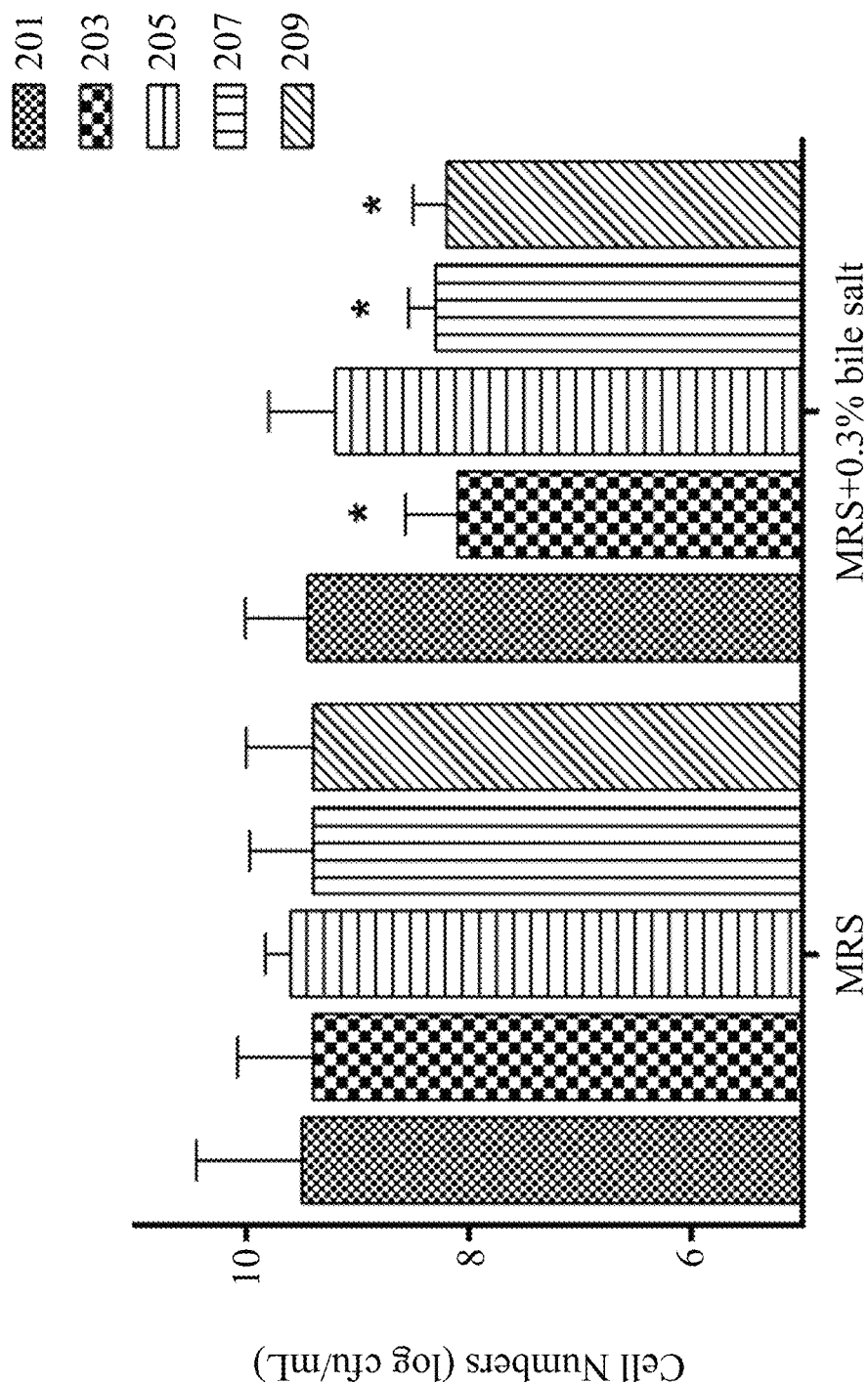
FIG. 2 shows the cell numbers of the bile tolerance test.

FIG. 2 showed the results of the bile tolerance test. The horizontal axis represented the concentration of bile salt in the medium, and the vertical axis represented the cell numbers of lactic acid bacteria strains. The bars 201, 203, 205, 207 and 209 represented the lactic acid bacteria strains GKK2, BCRC 17394, DSM 15954 (BB-12), ATCC SD 5220 (Bi 07) and ATCC SD 5219 (Bi 04), respectively. The symbols "*" represented a significant difference between GKK2 and the other lactic acid bacteria strains (p<0.05).

As FIG. 2 shown, the cell numbers of the strain GKK2 (bar 201) and the other four strains (bar 203, 205, 207 and 209) could reach to $5 \times 10^9$ cfu/mL when those strains were incubated in the original MRS liquid medium. For those incubated in the MRS liquid medium with 0.3% bile salt, the cell numbers of BCRC 17394 (bar 203), Bi07 (bar 207) and Bi04 (bar 209) were significantly lower than that of GKK2 (p<0.05), but there was no statistically significant difference in the cell numbers between BB-12 (bar 205) and GKK2. Accordingly, the viable cell numbers of the strain GKK2 were significantly higher than that of other strains in an environment of bile salts, indicating that GKK2 had a better bile resistance compared to that of the other strains, and thus when passing through the digestive tract in an organism's body, GKK2 was more resistant to bile slat.

Heat Tolerance Test

A total of five strains, GKK2, BCRC 17394 purchased from BCRC, *B. animalis* subsp. *Lactis* Bi 04 (deposited with an accession number of ATCC SD 5219 in ATCC), *B. animalis* subsp. *Lactis* BB-12 (deposited with an accession number of DSM 15954 in Leibniz-Institut DSMZ-Deutsche Sammlung von Mikroorganismen and Zellkulturen GmbH), and *B. animalis* subsp. *Lactis* Bi 07 (deposited with an accession number of ATCC SD 5220 in ATCC) were recovered. The strains were inoculated in the MRS liquid medium heated at 70° C. for respectively 5, 10 and 15 min, followed by serial dilution, spread plate, incubation and finally colony count and observed.

Figure 3:
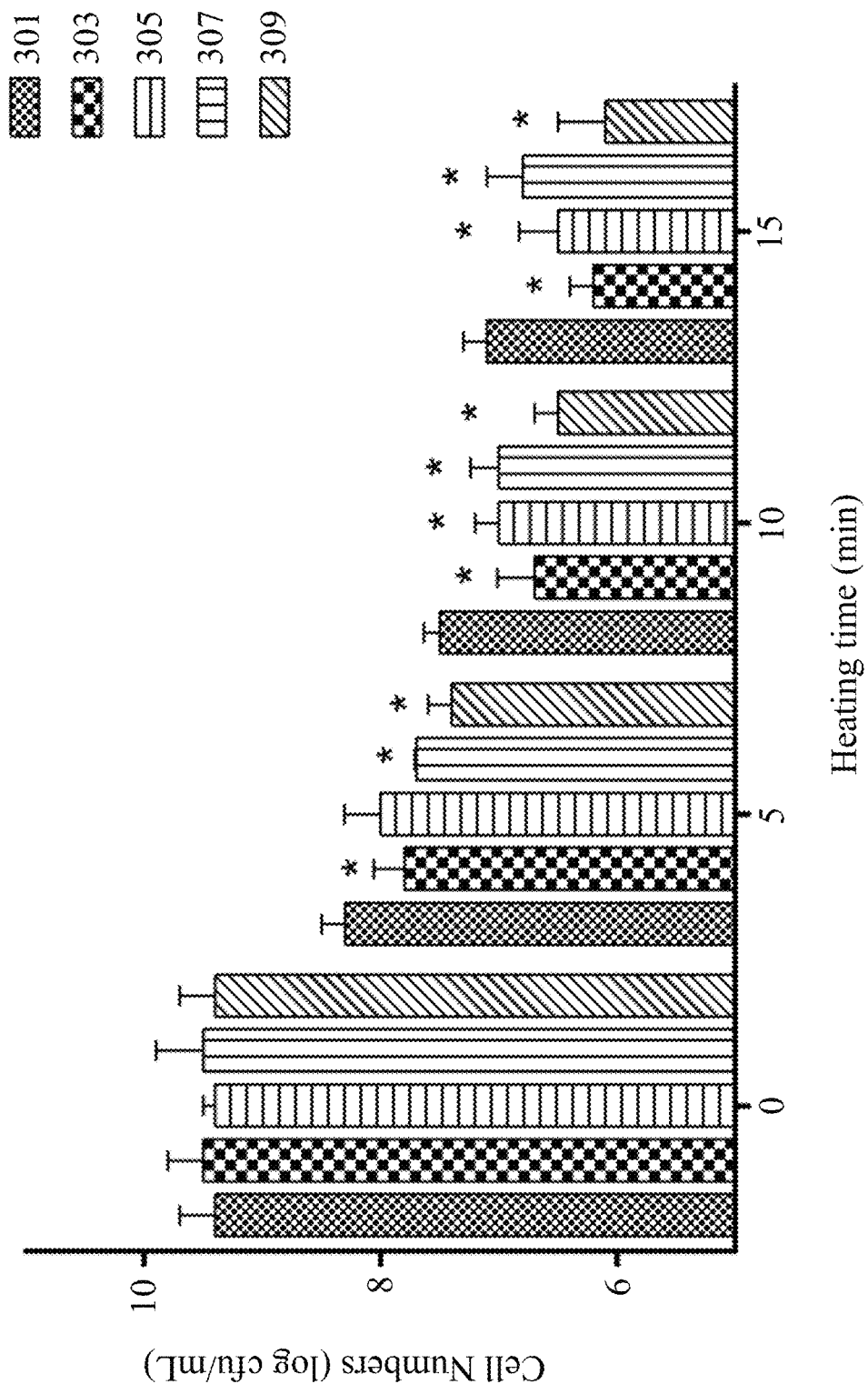
FIG. 3 shows the cell numbers of the heat tolerance test.

FIG. 3 showed the result of the heat tolerance test. The horizontal axis represented time lengths of 70° C. heating, and the vertical axis represented the cell numbers of lactic acid bacteria strains. The bars 301, 303, 305, 307, and 309 represented the lactic acid bacteria strains GKK2, BCRC 17394, DSM 15954 (BB-12), ATCC SD 5220 (Bi 07) and ATCC SD 5219 (Bi 04), respectively. The symbols * represented significant differences between GKK2 and the other lactic acid bacteria strains (p<0.05).

As shown in FIG. 3, the cell numbers of the strain GKK2 and that of the other four strains could reach $5 \times 10^9$ cfu/mL without being heated (0 min). When being heated at 70° C. for 5 min, the cell numbers of BCRC 17394 (bar 303), Bi07 (bar 307) and Bi04 (bar 309) were significantly lower than that of GKK2 (bar 301) (p<0.05), but there was no statistically significant difference in cell numbers between the strain BB-12 (bar 305) and the strain GKK2. When being heated at 70° C. for 15 min, the cell numbers of the four other strains were significantly lower than that of GKK2 (p<0.05). Accordingly, the viable cell number of GKK2 was significantly higher than that of the other strains in a high temperature environment, indicating that the heat resistance of GKK2 was better. While lactic acid bacteria were normally heat-labile and should be stored at low temperature to maintain the activities, this test showed that GKK2 had the characteristics of heat resistance and could be stored under room temperature for a long time, which was helpful to apply GKK2 in the development of processes.

Incubation of Strains

A isolated colony of each aforementioned lactic acid bacteria strains NOs. A to J was picked after streaking onto a solid medium. In a preferred embodiment, the solid medium was the MRS agar. The isolated colony was inoculated into a liquid medium contained in a flask to perform a liquid incubation step, thereby obtaining a liquid culture. In a preferred embodiment, the condition for the liquid culture was set at a temperature of 35 to 50° C., with ventilation in a range from zero to 1 vvm of $N_2$ or $CO_2$ and at a rotational speed in a range from 10 to 100 rpm. In a preferred embodiment, a time length of the liquid incubation step was from 16 to 24 hours, while 18 hours was more preferred. In a preferred embodiment, the liquid media was a MRS liquid medium. In a preferred embodiment, the liquid medium was made in a formula as shown in Table 2.

TABLE 2

Formula of Liquid Medium

| Ingredient | Ratio |
| --- | --- |
| Glucose | 1 to 10% |
| Yeast extract | 0.1 to 5% |
| Peptone | 0.1 to 5% |
| Micronutritions | 0.01 to 2% |
| Cysteine | 0.01 to 0.1% |
| Tween-80 | 0.05 to 1% |

Preparation of Lyophilized Powder

After the liquid incubation step, the liquid culture (the liquid medium including the bacteria) was gathered and centrifuged to obtain a pellet. In a preferred embodiment, the liquid culture was centrifuged at a rotation speed of 1000 to 15000 rpm. The obtained pellet was mixed with a protective agent (which included 6% to 30% skim milk powder) and lyophilized, followed by cryopreservation. In a preferred embodiment, a temperature for the lyophilization was set as −196° C. to −40° C. In a preferred embodiment, a time length of lyophilization was 16 to 72 hours. In a preferred embodiment, a temperature for cryopreservation was from −30° C. to 0° C. The lyophilized powder was used as a raw material the following cellular experiments, i.e., the lyophilized powder was one of the forms of the lactic acid bacteria having the active substances in the invention. Another form of the lactic acid bacteria having the active substances in the present invention also included the liquid culture obtained by performing the liquid incubation step on the aforementioned isolated colony.

Luciferase Reporter Assay on Cisd2 Gene

The lactic acid bacteria having the active substances affected the expression of the Cisd2 gene was determined by a luciferase reporter assay on Human Embryonic Kidney Cells (HEK) 293 cells (obtained from National Yang-Ming University, Taipei, Taiwan), whose luciferase reporter gene was controlled by a Cisd2 promoter to target Cisd2 gene. The HEK293 cells with the luciferase reporter genes were cultured in a 6-well plate with a cell density of $2 \times 10^5$ cell/mL and incubated at 37° C. temperature in a 5% $CO_2$ incubator for one day. Then, the aforementioned prepared lyophilized powders of lactic acid bacteria strains NOs. A to J were recovered with a carrier of 0.1% DMSO to prepare solutions containing different concentrations of the lyophilized powders listed in Table 3, and then added to a culture medium of the HEK293 cells as experimental groups. For a control group, the HEK293 cells were merely treated with the carrier of 0.1% DMSO. The HEK293 cells were co-incubated with either the lactic acid bacteria having the active substances or the carrier 0.1% DMSO at 37° C. temperature in the 5% $CO_2$ incubator for 24 hours. Finally, luciferase activities of the HEK293 cells were measured and analyzed quantitatively. The luciferase reporter assay was repeated three times. Experimental results were shown in FIG. 4.

TABLE 3

Concentration of Lyophilized Powder of Lactic Acid Bacteria Strains NOs. A to J

| NO. | Concentration 1 (μg/mL) | Concentration 2 (μg/mL) |
| --- | --- | --- |
| A | 12.5 | 25 |
| B | 5 | 10 |
| C | 0.25 | 0.5 |
| D | 0.75 | 1.5 |
| E | 1.25 | 2.5 |
| F | 0.75 | 1.5 |
| G | 6.25 | 12.5 |
| H | 0.75 | 1.5 |
| I | 2.5 | 5 |
| J | 25 | 50 |

Expression Level of Endogenous Cisd2 Gene

The lactic acid bacteria having the active substances that affect the Cisd2 gene expression was confirmed by detecting the expression level of the endogenous Cisd2 gene. Firstly, the HEK293 cells were inoculated in the 6-well plates with the cell density of $2 \times 10^5$ cell/mL and incubated at 37° C. in the 5% $CO_2$ incubator for one day. Then, the lyophilized powders of the six lactic acid bacteria strains NOs. A, B, C, D, H and I were recovered with the carrier of 0.1% DMSO, made into solutions with different concentrations as listed in Table 4 and applied to the culture medium of the HEK293 cells as experimental groups. For a control group, the culture medium of the HEK293 cells was treated merely with the carrier of 0.1% DMSO. The HEK293 cells were co-incubated with either the lactic acid bacteria having the active substances or the carrier at 37° C. in the 5% $CO_2$ incubator for 24 hours. The HEK293 cells were scraped from the 6-well plates on ice, and then mRNA was extracted with a commercially available RNA purification kit (GeneJET RNA Purification Kit, Thermo Fisher Scientific, Cat. #K0731, MA, USA). After diluted into a proper concentration, the mRNA was reversely transcribed into cDNA by an RNA reverse transcription kit (RevertAid H Minus First Standard cDNA Synthesis Kit, Thermo Fisher Scientific, Cat. #K1632, MA, USA). Finally, the expression level of the endogenous Cisd2 gene was analyzed by PCR. An electrophoresis image of experimental results was shown as FIG. 5, and the analysis result of FIG. 5 was shown in FIG. 6.

TABLE 4

Concentration of Lyophilized Powders of Lactic Acid Bacteria Strains NOs. A, B, C, D, H and I

| NO. | Concentration 1 (μg/mL) | Concentration 2 (μg/mL) | Concentration 3 (μg/mL) |
|---|---|---|---|
| A | 12.5 | 25 | N/A |
| B | 5 | 10 | N/A |
| C | 0.25 | 0.5 | N/A |
| D | 0.75 | 1.5 | N/A |
| H | 0.75 | 1.5 | 5 |
| I | 2.5 | 5 | 10 |

Statistical Methods for Experiments Related to Cisd2

All the data were shown as mean±standard deviation (SD). Fold changes were the changes of the gene activities compared between the control group and the experimental group. When there were statistically significant differences between the experimental group and the control group, *$p<0.05$ was a statistically significant difference and **$p<0.01$ was an extremely statistically significant difference.

Results of Cisd2 Experiments

Figure 4:
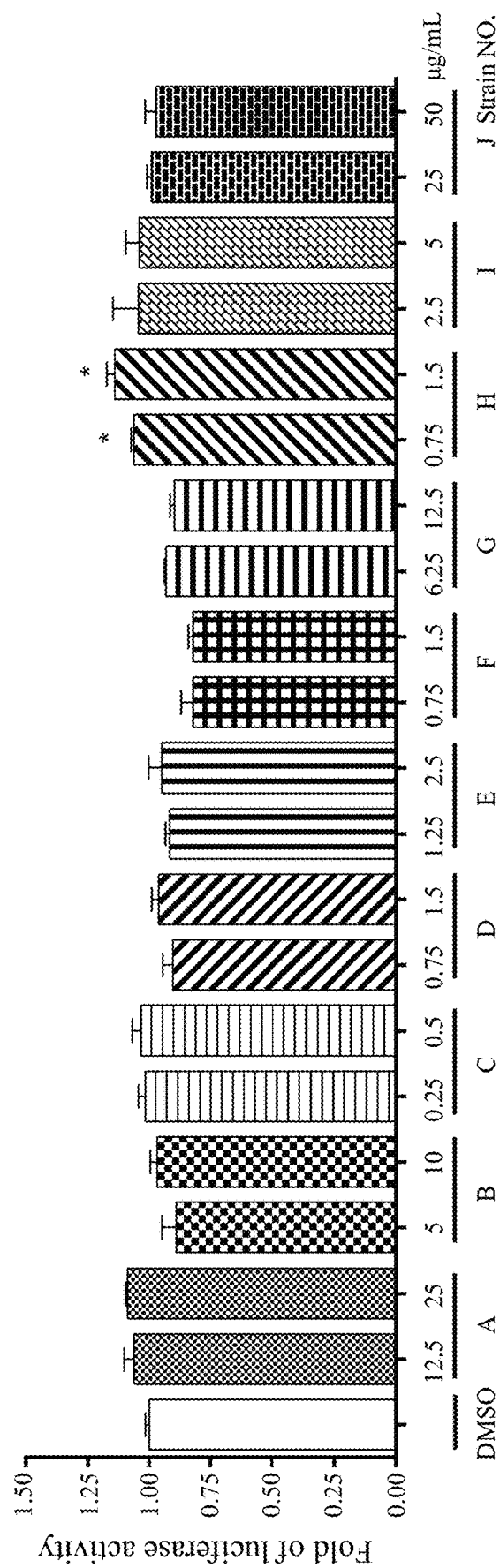
FIG. 4 shows the relative activity of the luciferase reporter gene controlled by the Cisd2 promoter in the HEK293 cells treated with different doses of a composition comprising lactic acid bacteria strains NOs. A to J having active substances.

FIG. 4 showed the experimental results of the luciferase reporter assay targeting Cisd2. The horizontal axis represented the treatment and the vertical axis represented the fold of luciferase activity of the experimental group compared to that of the control group. Among the HEK293 cells treated with ten lactic acid bacteria strains NOs. A to J having the active substances, those treated with the lactic acid bacteria strains NOs. A, C, H or I showed higher luciferase activities than that of the control groups which suggested their ability to enhance the expression of Cisd2 gene. Particularly, the luciferase activities of the HEK293 cells treated with strain NO. A at either concentration of 12.5 μg/mL or higher concentration of 25 μg/mL were higher than that of the control group. The result indicated that the lactic acid bacteria strain NO. A having the active substances could activate Cisd2 gene and stimulate the expression of Cisd2 gene. The results showed that the HEK293 cells in the experimental group treated by 0.25 μg/mL or 0.5 μg/mL strain NO. C, similar to those treated by strain NO. A, had luciferase activities higher than that of the control group. The result also indicated that lactic acid bacteria strain NO. C having the active substances could activate the Cisd2 gene and stimulate the expression of Cisd2 gene. For the HEK293 cells in the experimental group treated with 1.5 μg/mL strain NO. H, the luciferase activity of the treated HEK 293 cells was about 1.14-fold of that of the control group. The result also proved that the lactic acid bacteria strain NO. H having the active substances could significantly activate Cisd2 gene ($p<0.05$) and also had the potential to stimulate the expression of Cisd2 gene. The HEK293 cells treated with the either 2.5 μg/mL or 5 μg/mL lactic acid bacteria strain NO. I having the active substance also showed higher luciferase activities when compared to that of the HEK293 cells in the control group, indicating that the lactic acid bacteria strain NO. I having the active substance also had the potential to activate the expression of the Cisd2 gene.

Figure 5:
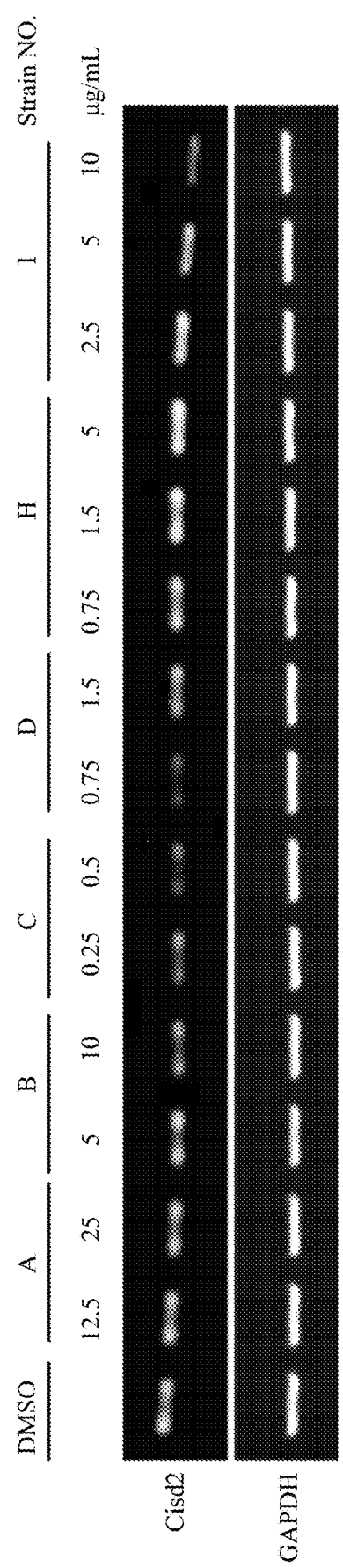
FIG. 5 is the electrophoresis image of the expression level of endogenous Cisd2 mRNA in the HEK293 cells treated with different doses of the composition comprising of lactic acid bacteria strains NOs. A, B, C, D, H, I having the active substances.
Figure 6:
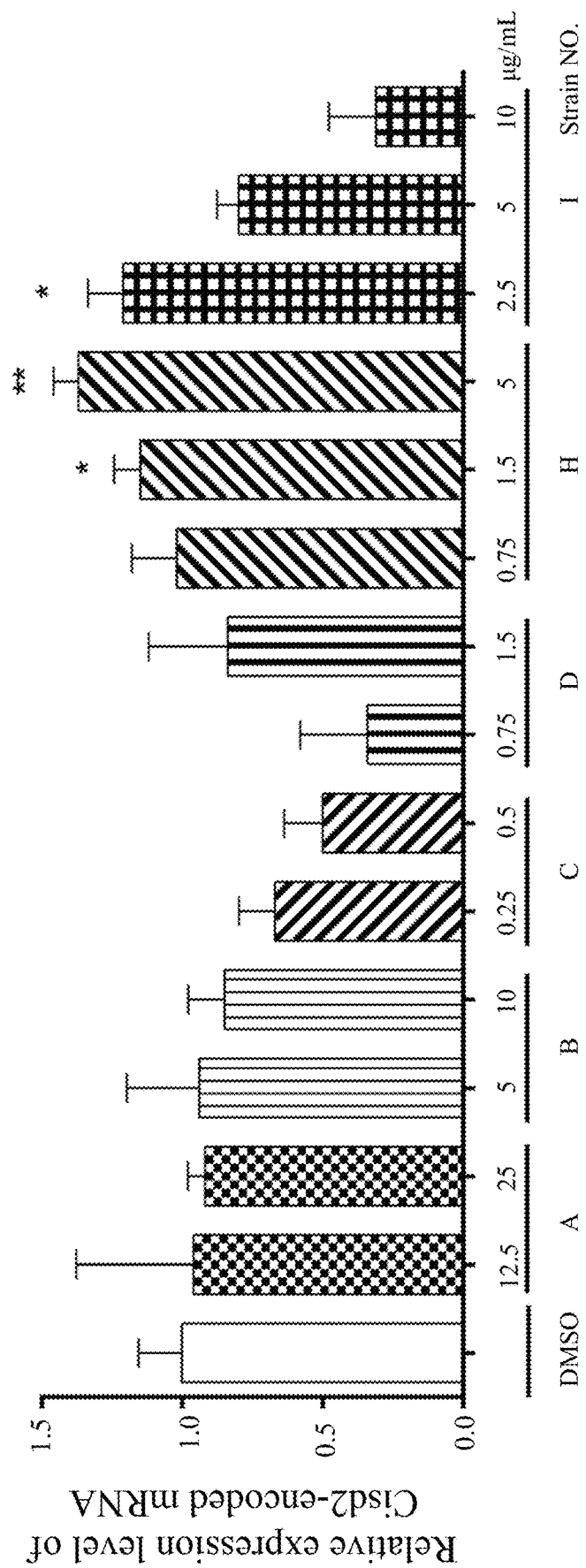
FIG. 6 is the statistical result of the relative expression level of Cisd2 mRNA based on the result of FIG. 5.

The experimental results for the expression levels of the endogenous Cisd2 gene were shown in FIG. 5 and FIG. 6. The expression levels of Cisd2 mRNA of the HEK293 cells in the experimental group treated with the strains NOs. A and C were not significantly higher than that of the control group. Particularly, the HEK293 cells in the experimental group treated with the strain NO. C was even lower than that of the control group. Moreover, the expression levels of Cisd2 mRNA of the HEK293 cells treated with either 1.5 μg/mL strain NO. H, 5 μg/mL strain NO. H or 2.5 μg/mL strain NO. I in the experimental groups were significantly higher than that of the control group, indicating that the lactic acid bacteria strains NOs. H and I could enhance the expression levels of Cisd2 mRNA. Specifically, after the HEK293 cells treated with 1.5 μg/mL and 5 μg/mL strain NO. H, the expression level of Cisd2 mRNA was stimulated to about 1.15-fold ($p<0.05$) and 1.37-fold ($p<0.01$), respectively, when compared with the control group. The expression level of the endogenous Cisd2 gene increased as the concentrations of the lactic acid bacteria having active substances increased, indicating a concentration-effect relation. 2.5 μg/mL lactic acid bacteria strain NO. I could stimulate the expression level of Cisd2 mRNA to about 1.21-fold ($p<0.05$) compare with the control group.

The aforementioned experimental results proved that only specific lactic acid bacteria strains having the active substances (the preferred embodiments were *Lactobacillus paracasei*, *Lactobacillus plantarum* or *Bifidobacterium lactis*) increased the expression level of the longevity gene, Cisd2. Based on these results, a new application of the lactic acid bacteria was discovered in the medicinal field. Accordingly, to enable the lactic acid bacteria having the active substances to be applied in practice, a composition including the lactic acid bacteria having the active substances was made and subjecting to a subject with an effective dose to reach the wanted effects.

The following experiments were conducted to evaluate the age-delaying and longevity-promoting effects of the lactic acid bacteria strain NO. I (GKK2).

Animal Experiment for Aging Evaluation

Figure 7:
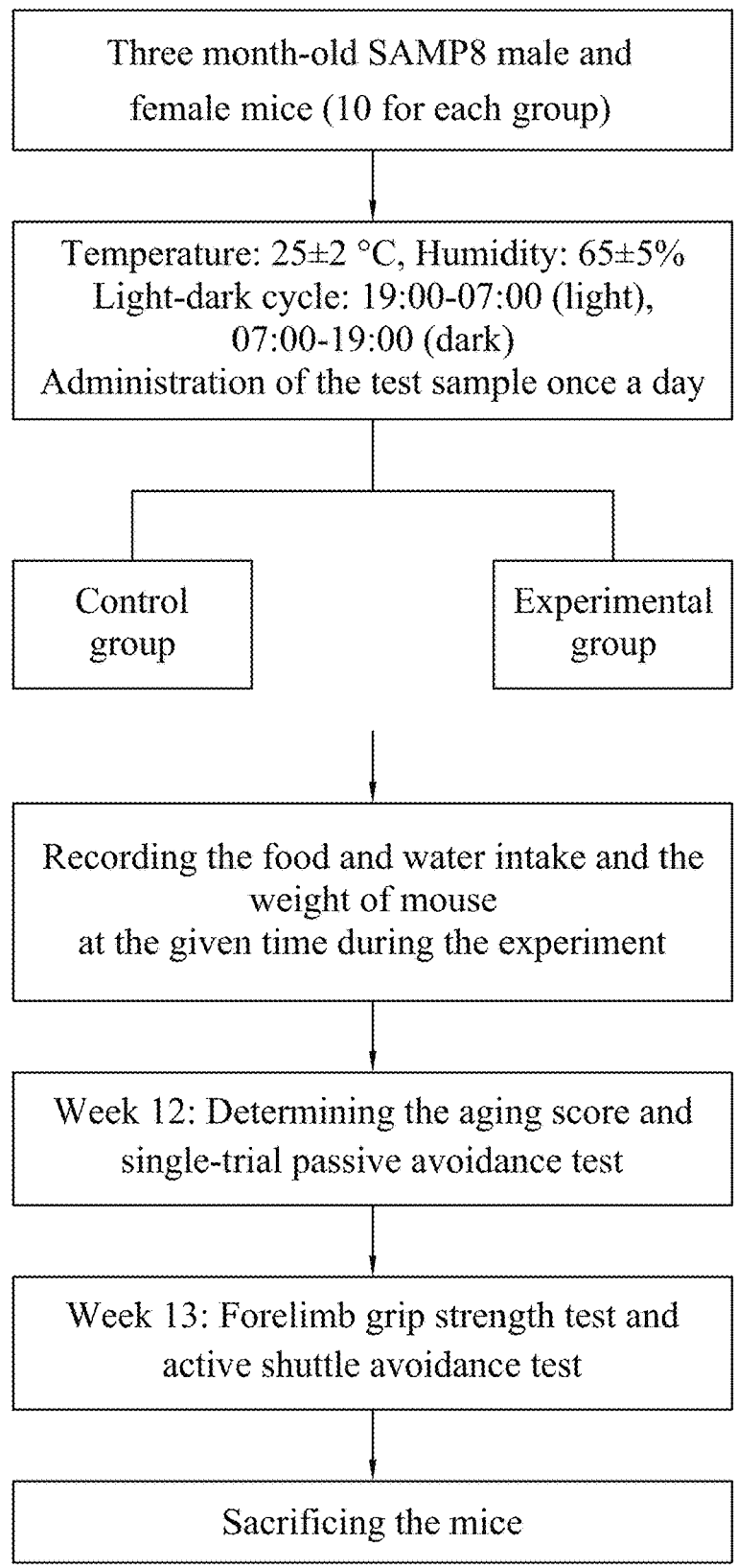
FIG. 7 shows the flow chart of the animal experiment.

A process of the following experiments was shown in FIG. 7. In the experiments, senescence-accelerated mice (SAM) were employed to establish an animal model of accelerated aging. The SAM mice were developed by T. Takeda's team, Tokyo University, Tokyo, Japan, and represent a sub-strain of AKR/J mice produced through a program of selective breeding. The line of SAM mice for the experiments was SAMP8, which was characterized by the loss of brain neurons, cortical atrophy, lipofuscin, cavernous malformation in the reticular formation, and amyloid deposition. Other characteristics of the SAMP8 mice included accelerated aging of other organs and reduced lifespan. Therefore, the SAMP8 mice were an ideal animal model for studies related to delaying aging and reproduction. The SAMP8 mice were kept in 30 (W)×20 (D)×10 (H) cm$^3$ transparent plastic cages located in an animal facility with a temperature maintaining at 25±2° C. and a humidity maintaining at 65±5% in an automatically controlled free-dust room. A light-dark cycle was controlled by an automatic timer set from 7:00 to 19:00 as the dark period and 19:00 to 7:00 as the light period.

Referring to "Methods to Assess Health Benefits of Health Food for Delaying aging" announced by the Ministry of Health and Welfare of Taiwan, the three month-old male and female SAMP8 mice was selected as the experimental animals in the following experiments. Twenty male and twenty female mice were grouped into a control group (n=10) and an experimental group administered with the lactic acid bacteria strain NO. I (n=10). While the mice in the control group were administered by ddH$_2$O, the mice in the experimental group were administered with the lyophilized powder of lactic acid bacteria strain NO. I (GKK2) recovered in ddH$_2$O as test samples with wanted doses. The details of the groups and the wanted doses of the test sample were listed in Table 5.

TABLE 5

| Group | Test sample (lactic acid bacteria strain NO. I(GKM3)) | Dose |
| --- | --- | --- |
| Control group | ddH$_2$O | 10 mL/day |
| Experimental group | Lyophilized powder of lactic acid bacteria strain | 5.1 × 10$^9$ cfu/kg body weight (BW)/day |

The process of experiments lasted for 13 weeks. During the experiment, the mice were administered once per day, and intakes of food and water of the mice were recorded every day. An aging score determination and a single-trial passive avoidance test were performed on the 12$^{th}$ week. A forelimb grip strength test and an active shuttle avoidance test were performed on the 13$^{th}$ week. After completing the test, the mice were anesthetized by carbon dioxide and sacrificed by decapitation (the mice fast for 8 hours before being sacrificed). The blood and organs were taken for further analysis.

Aging Score

The aging score, formulated by Takeda, et al. in 1981, was adapted to determinate aging degrees of the SAM mice. Six following items were selected for aging degree determination: skin glossiness, coarseness, hair loss, skin ulceration, periophthalmic lesions and lordokyphosis of the spine. In an assessment, aging scores of each item were 0, 1, 2, 3 and 4 from low to high aging degree. The aging score of each item was added together after the assessment, and the mice with the higher aging scores had a higher aging degree.

Forelimb Grip Strength Test

During the process of aging, physiological functions of a person were gradually degenerated. Moreover, the person might have multiple chronic diseases, which lead to decreased activities that trigger muscle disuse atrophy. Generally speaking, the person lost 1 to 2% of muscle masses per year after 30 years old, and a rate of muscle mass loss dramatically increased after 60 years old, which could even reach to about 15% per year. The loss of the muscle mass was a risk factor of afterward adverse health events such as disability, falls, functional degeneration, long-term bedridden and even death.

Following aging was a skeletal muscle loss, which becomes sarcopenia. The sarcopenia was discussed from three respects: (1) the low muscle masses, (2) a low muscle strength, and (3) a low physical performance. The European Working Group on Sarcopenia in Older People developed a diagnostic method and a definition for the aging-related sarcopenia in 2010. Those elderly over 65 years old were diagnosed to have the sarcopenia with a habitual gait speed lower than 1.0 m/s or low handgrip strength, as well as the muscle masses less than a critical value. According to statistical data of an elderly enrollment of the Division of General Medicine and the Division of Family Medicine of National Taiwan University Hospital, prevalence rates of the sarcopenia increased from 18% to 64% for men and from 9% to 41% for women as they get older. However, deterioration of the sarcopenia and physical weakness could be delayed by effective intervention and diagnosis to prevent any adverse health event from happening afterward.

In the forelimb grip strength test, an Ugo Basil Grip-Strength Meter (GSM, Cat. #47200, Ugo Basile, 21036 VA, Italy) was used to test forearm grip strengths of the SAMP8 mice for muscle strength evaluation. In the test, each mouse was held on its tail at the endpoint so that the mouse could grip a grasping bar with its forelimbs. Then, the tail was pulled backwardly in a horizontal way until the mouse let go of the grasping bar. Results were continuously recorded three times by the GSM.

Single-Trial Passive Avoidance Test

The lactic acid bacteria that could affected learning and memory of the mice was determined by the single-trial passive avoidance test, which was based on a classical conditioning principle and a negative phototaxis habit of mice. A special box used in the experiment had a gate at the center separating the box into a bright chamber and a dark chamber connecting to each other. At the bottom of the box were metal rods arranged in parallel and connected to a current. The mice were first placed in the bright room and was then allowed to as discover freely after the gate at the center opened when the single-trial passive avoidance test started. Once the mice stepped into the dark chamber, the gate was closed immediately, and 0.5 mA single electrical shock was given to the mice for 0.5 sec as a learning training. The learning and memory of the mice were tested at 24, 48, and 72 hours after training by the same operating way without giving the electric shocks, and latency times of the mice staying in the bright chamber were recorded. The maximum testing time length was 180 sec. Learning and memory of the mice were evaluated by the latency times of the mice in the bright chamber. The longer latency times of the mice in the bright room represented better learning and memory of the mice.

Active Shuttle Avoidance Test

The lactic acid bacteria that affected the learning and memory of the mice were determined having the active shuttle avoidance test based on the classical conditioning principle and the mice habits of the negative phototaxis and a phonotaxis. The special box used in the test had the gate at the center separating the box into the bright chamber and the dark chamber connecting to each other, and had the metal rods arranged in parallel connected to the current device at the bottom. Timings of light, noise or the electric shocks were controlled by a computer program. First, conditioned stimuli (CS) of the light and the sound were given to the mice. For those who do not avoid the CS, the electric shock was given as an unconditioned stimulus (UCS). For those who avoided the CS, the electric shock was not given. The experimental animals were tested by the CS/UCS of the active shuttle avoidance test five times per trial, four trials per day for four days continuously. The learning and memory of the mice active was evaluated by the shuttle avoidance test with the successful active avoidance times of the mice in the system. More successful active avoidance times of the mice represented better learning and memory of the mice.

Statistical Methods for Animal Experiments

The data obtained by the studies were statistically analyzed with package statistic software Statistical Product and Service Solutions (SPSS), and values of the experimental results were showed as mean±standard deviation of the sample means (SEM). The data were tested by one-way analysis of variance (one-way ANOVA) to test differences between groups and by Duncan's Multiple Range Test (MRT) to test differences within each group. *$p<0.05$ indicated a statistically significant difference.

Results of Animal Experiments

The aging score for each group was shown in Table 6 and Table 7.

TABLE 6

Aging Score of Female Mice

| Items | Control group | Experimental group |
|---|---|---|
| Skin | | |
| Glossiness | $1.00 \pm 0.00^a$ | $0.30 \pm 0.15^d$ |
| Coarseness | $0.90 \pm 0.10^a$ | $0.60 \pm 0.16^c$ |
| Hair loss | $0.50 \pm 0.17^a$ | $0.00 \pm 0.00^b$ |
| Ulceration | $0.00 \pm 0.00$ | $0.00 \pm 0.00$ |
| Eye | | |
| Periophthalmic lesions | $1.50 \pm 0.22^a$ | $0.90 \pm 0.18^b$ |
| Spin | | |
| Lordokyphosis of the spine | $1.00 \pm 0.00^a$ | $0.50 \pm 0.17^b$ |
| Total | $4.90 \pm 0.23^a$ | $2.30 \pm 0.37^b$ |

Values were expressed as mean ± S.E.M. and analyzed by one-way ANOVA. (n = 10)
*The scores with the same superscript were not significantly different within the group.

TABLE 7

Aging Score of Male Mice

| Items | Control group | Experimental group |
|---|---|---|
| Skin | | |
| Glossiness | $0.50 \pm 0.17$ | $0.20 \pm 0.13$ |
| Coarseness | $0.80 \pm 0.13$ | $0.50 \pm 0.17$ |
| Hair loss | $0.20 \pm 0.13$ | $0.00 \pm 0.00$ |
| Ulceration | $0.00 \pm 0.00$ | $0.00 \pm 0.00$ |
| Eye | | |
| Periophthalmic lesions | $0.80 \pm 0.13$ | $0.30 \pm 0.15$ |
| Spin | | |
| Lordokyphosis of the spine | $0.70 \pm 0.15$ | $0.40 \pm 0.16$ |
| Total | $3.00 \pm 0.33^a$ | $1.40 \pm 0.34^b$ |

Values were expressed as mean ± S.E.M. and analyzed by one-way ANOVA. (n = 10)
*The scores with the same superscript were not significantly different within the group.

Referring to the aforementioned aging score on the $12^{th}$ week, there were statistically significant differences in the aging scores between the control group and the experimental group, in which both three month-old male and female SAMP8 mice were treated with the lactic acid bacteria strain NO. I (GKK2). In particular, the differences were more significant between female mice (p<0.05). Since higher aging scores (the total scores shown in Table 6 and Table 7) represented higher aging degree, the aging scores obtained from the animal experiments showed that administering the mice with lactic acid bacteria strain NO. I (GKK2) beneficially decreased the aging degree of the mice, indicating that the lactic acid bacteria strain NO. I (GKK2) had a significant effect on delaying aging.

Figure 8:
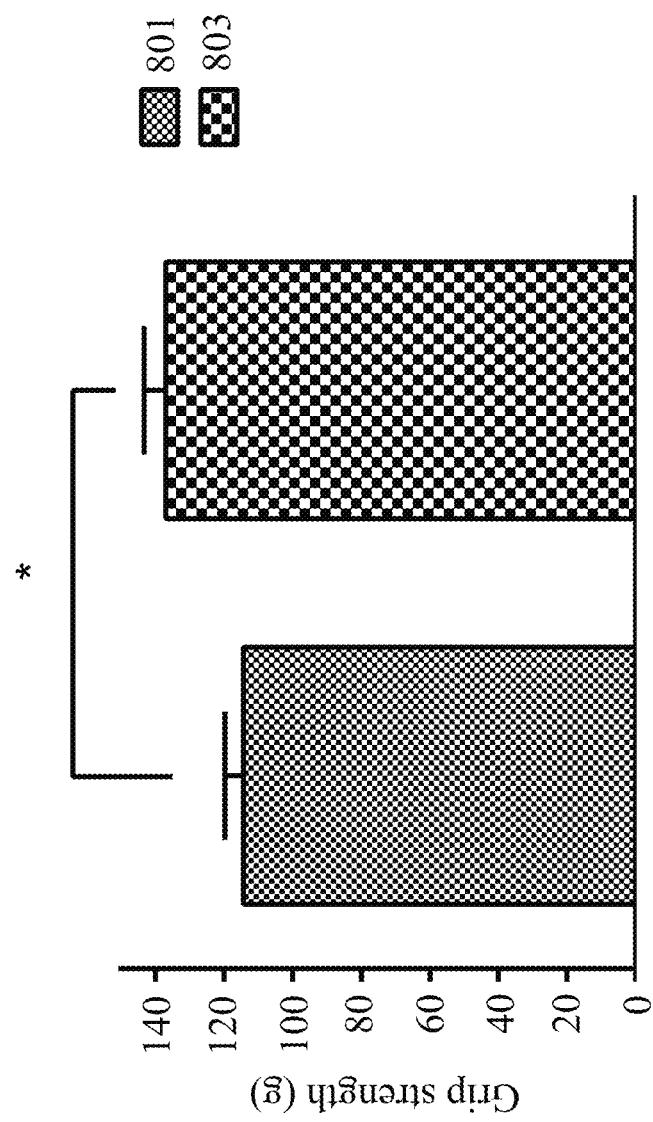
FIG. 8 shows the grip strength of male mice in the forelimb grip strength test.

The result of the forelimb grip strength test of the male mice in each group was shown in Table 8, and the statistical analysis was shown in FIG. 8, of which the vertical axis represented the grip strength, the horizontal axis represented the groups, and bars 801 and 803 represented the control group and the experimental group, respectively.

TABLE 8

Result of Forelimb Grip Strength Test of Male Mice

| Group | Grip strength (g) |
|---|---|
| Control | 114.4 ± 5.43 |
| Experimental | 137.04 ± 6.26 |

Values were expressed as mean ± S.E.M. and analyzed by one-way ANOVA. (n = 10)
*The scores with the same superscript were not significantly different within the group.

Referring to the grip strengths measured in the aforementioned forelimb grip strength test on the 13th week, the grip strengths of the mice in the experimental group administered with the lactic acid bacteria strain NO. I (GKK2) (bar 803) were significantly higher (p<0.05) than that of the mice in the control group (bar 801). Since higher grip strength indicated better muscle strength, the results showed that the mice administered with the lactic acid bacteria strain NO. I (GKK2) had better muscle strengths, indicating that the lactic acid bacteria strain NO. I (GKK2) had a significant effect on alleviating the sarcopenia caused by aging.

Figure 9:
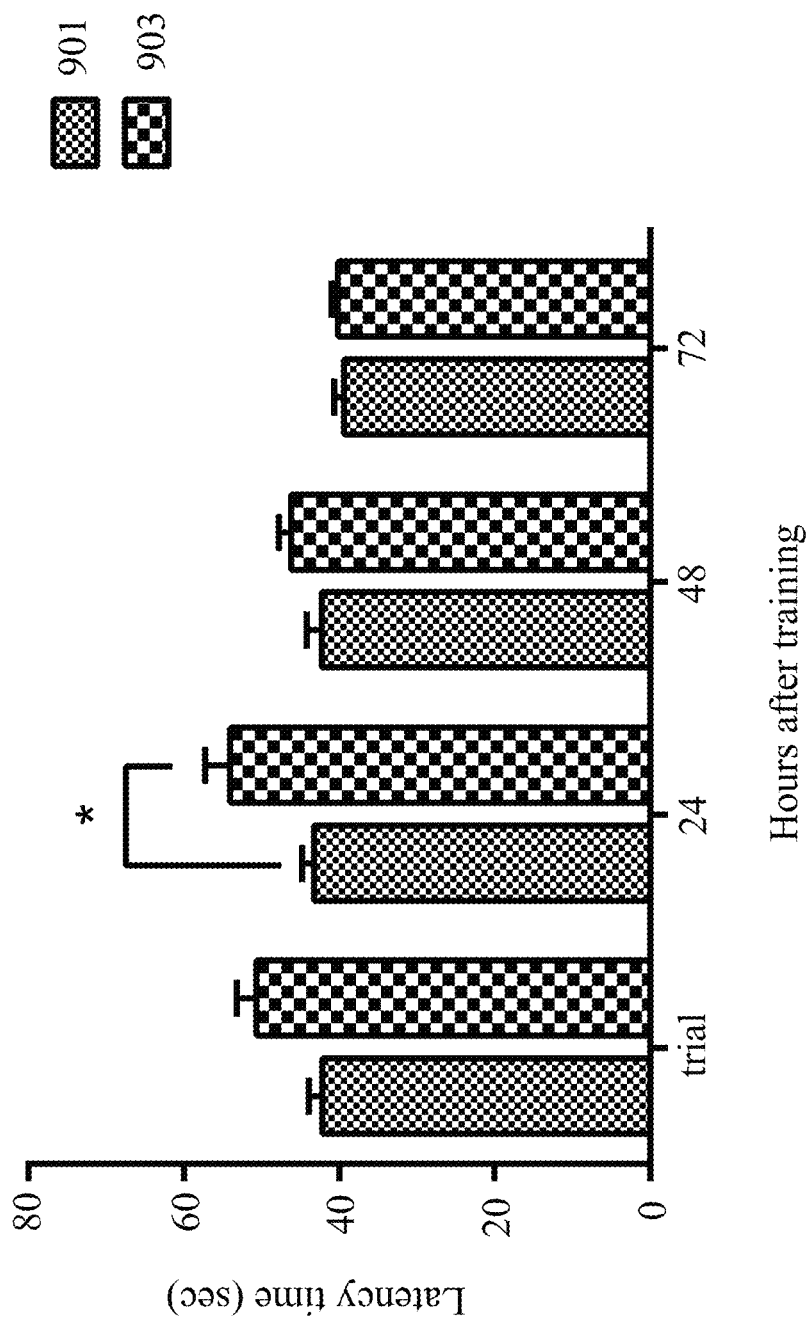
FIG. 9 shows the latency time of female mice in the single-trial passive avoidance test.
Figure 10:
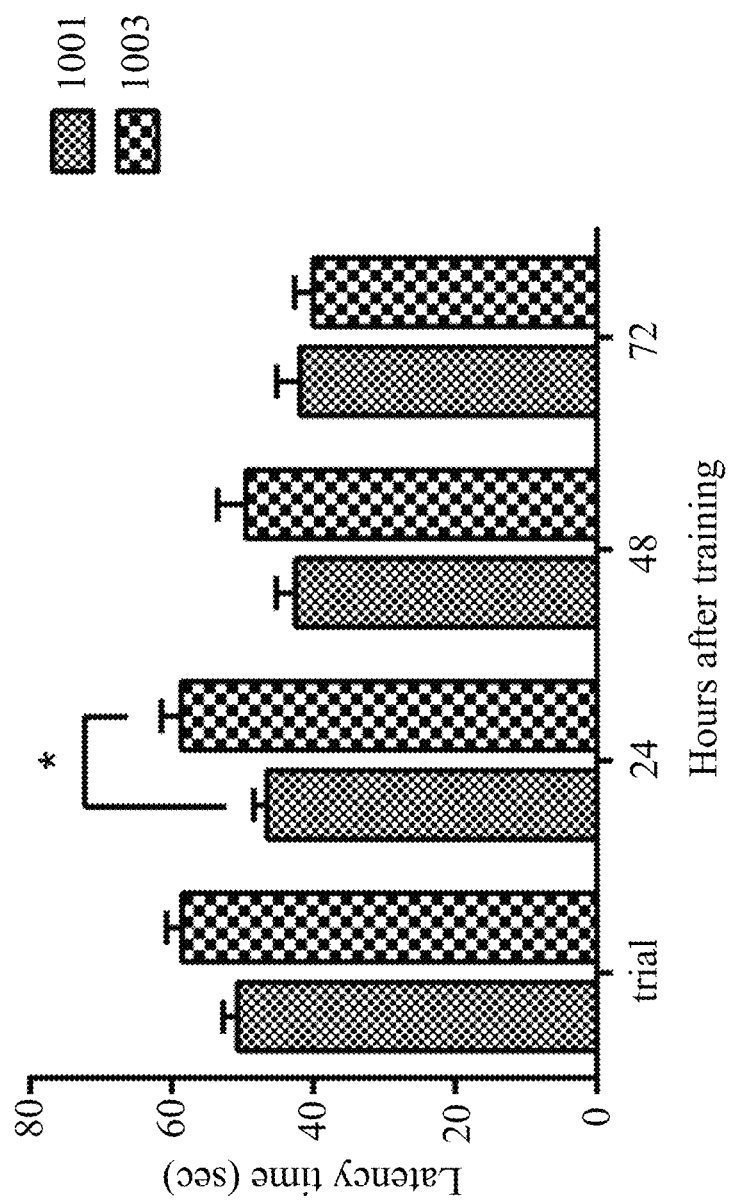
FIG. 10 shows the latency time of male mice in the single-trial passive avoidance test.

For the single-trial passive avoidance test, the experimental results and the statistical analyses of the female and male mice in each group were shown in Table 9, FIG. 9 and Table 10, FIG. 10, respectively. In FIGS. 9 and 10, the horizontal axes represented the time after training, while the vertical axes represented the latency time, and bars 901/1001 and 903/1003 represented the control group and the experimental group, respectively.

TABLE 9

Result of Single-Trial Passive Avoidance Test for Female Mice

| Groups | Latency time (sec) | | | |
|---|---|---|---|---|
| | Trial | 24 hours | 48 hours | 72 hours |
| Control | 50.80 ± 1.99 | 46.60 ± 1.85 | 42.60 ± 2.72 | 41.90 ± 3.31 |
| Experimental | 58.60 ± 2.20 | 58.70 ± 2.79* | 49.60 ± 3.98 | 40.00 ± 2.71 |

Values were expressed as mean ± S.E.M. and analyzed by one-way ANOVA. (n = 10)
*denotes the significant differences between the control group and the experimental group (p < 0.05)

TABLE 10

Result of Single-Trial Passive Avoidance Test for Male Mice

| Groups | Latency time (sec) | | | |
|---|---|---|---|---|
| | Trial | 24 hours | 48 hours | 72 hours |
| Control | 42.20 ± 1.78 | 43.30 ± 1.51 | 42.30 ± 1.93 | 39.40 ± 1.28 |
| Experimental | 50.70 ± 2.56 | 54.10 ± 3.17* | 46.20 ± 1.65 | 40.20 ± 0.84 |

Values were expressed as mean ± S.E.M. and analyzed by one-way ANOVA. (n = 10)
*denotes the significant differences between the control group and the experimental group (p < 0.05)

Referring to the result of the single-trial passive avoidance of the mice on the 13th week, both three month-old male and female SAMP8 mice showed there were statistically significant differences in the latency time between the control group (bar 1001, bar 901) and the experimental group, in which the mice were administered with the lactic acid bacteria strain NO. I (GKK2) (bar 1003, bar 903). Moreover, the difference in the mice latency time was more significant at the 24th hours after the learning training. Since longer latency time indicated better learning and memory of the mice, the result showed that the mice administered with the lactic acid bacteria strain NO. I (GKK2) samples had better learning and memory, indicating that the lactic acid bacteria strain NO. I (GKK2) had a significant effect on delaying aging.

Figure 11:
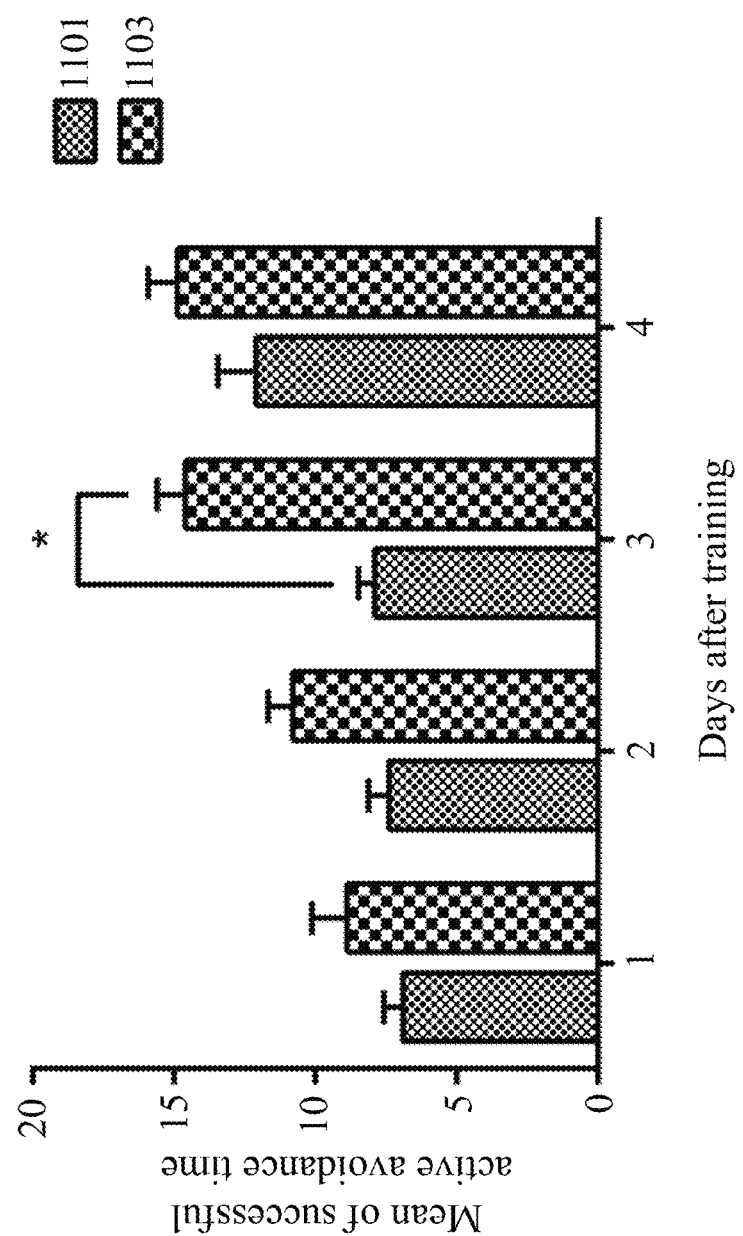
FIG. 11 shows the mean successful active avoidance times of female mice in the active shuttle avoidance test.
Figure 12:
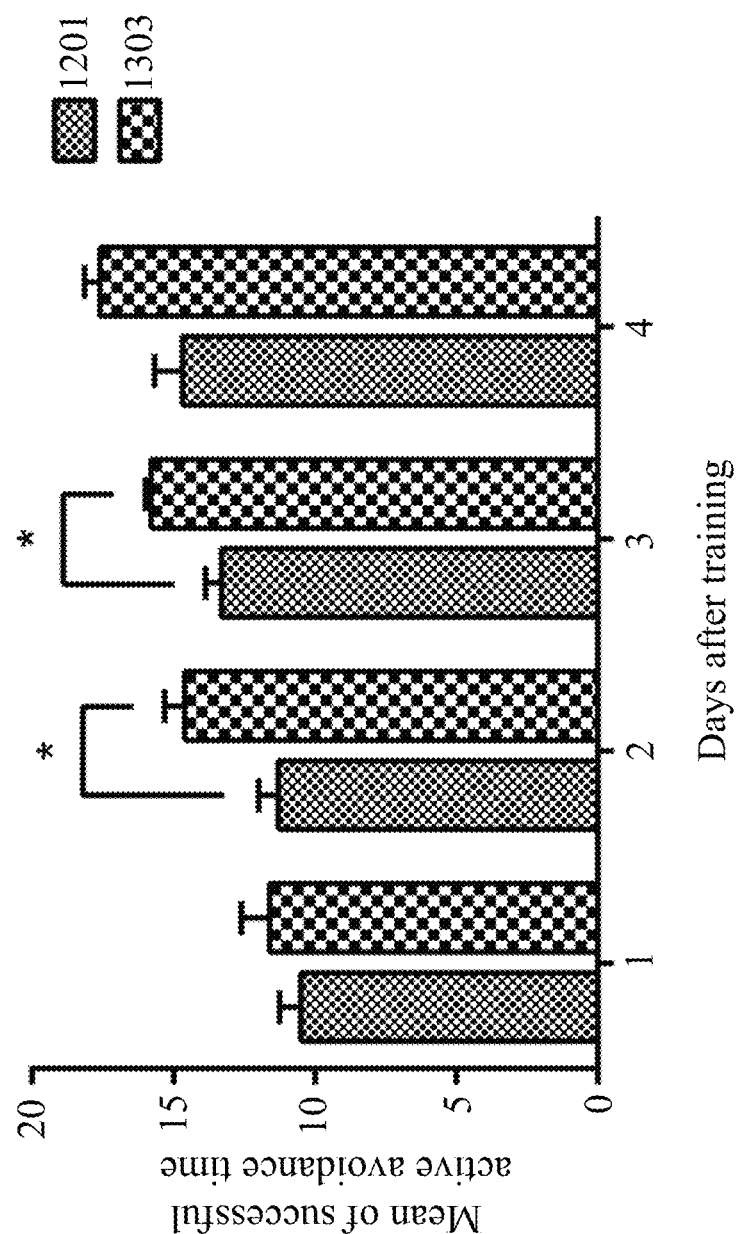
FIG. 12 shows the mean successful active avoidance times of male mice in the active shuttle avoidance test.

For the active shuttle avoidance test, the experimental results and statistical analysis of each group of the female mice were shown in Table 11 and FIG. 11, respectively. The experimental results and statistical analysis of each group of the male mice were shown in Table 11 12 and FIGS. 11 12, respectively. In FIGS. 11 and 12, the horizontal axes represented days after training, the vertical axes represented mean of successful active avoidance time, and bars 1101/1201 and 1103/1203 represented the control groups and the experimental groups, respectively.

TABLE 11

Results of Active Shuttle Avoidance Test for Female Mice

| Group | Mean of successful active avoidance time | | | |
|---|---|---|---|---|
| | Day 1 | Day 2 | Day 3 | Day 4 |
| Control | 6.90 ± 0.69 | 7.40 ± 0.75 | 7.90 ± 0.59 | 12.10 ± 1.36 |
| Experimental | 8.90 ± 1.25 | 10.80 ± 0.90 | 14.60 ± 1.00* | 14.90 ± 1.03 |

Values were expressed as mean ± S.E.M. and analyzed by one-way ANOVA. (n = 10)
*denotes the significant differences between the control group and the experimental group ($p < 0.05$)

TABLE 12

Results of Active Shuttle Avoidance Test for Male Mice

| Group | Mean of successful active avoidance time | | | |
|---|---|---|---|---|
| | Day 1 | Day 2 | Day 3 | Day 4 |
| Control | 10.50 ± 0.75 | 11.30 ± 0.70 | 13.30 ± 0.58 | 14.70 ± 0.97 |
| Experimental | 11.60 ± 1.00 | 14.60 ± 0.72* | 15.80 ± 0.21* | 17.60 ± 0.56 |

Values were expressed as mean ± S.E.M. and analyzed by one-way ANOVA. (n = 10)
*denotes the significant differences between the control group and the experimental group ($p < 0.05$)

Referring to the successful active avoidance times of the mice in the active shuttle avoidance test on the $14^{th}$ week, there were no statistically significant differences in the successful active avoidance times between each group on the first experimental day after a trail since they were still in a process of learning. However, on the second to fourth day after the trail, the successful active avoidance times of both male and female mice of the experimental group (bars 1203, 1103, respectively) were significantly higher than that of the control group (bar 1201, 1101, respectively). Particularly, the successful active avoidance times of the female mice in the experimental group were twice higher than that of the control group ($p<0.05$) on the third day after the trail. Since more successful active avoidance times indicated better learning and memory of the mice, the result showed that the learning and memory of those administered with the lactic acid bacteria strain NO. I (GKK2) samples were better. From the aforementioned results, the lactic acid bacteria strain NO. I (GKK2) was proved to have a significant effect on alleviating the deteriorating learning and memory resulted from aging-related neurodegenerative diseases.

From the result of the aforementioned experiment, the lactic acid bacteria, especially *Bifidobacterium lactis*, or the preferred one, the lactic acid bacteria strain NO. I (GKK2) significantly improved the expression level of the longevity gene Cisd2, the aging score, the forelimb grip strength test, as well as learning and memory. Thus, the compositions comprising the lactic acid bacteria strain NO. I (GKK2) having the active substances could be applied for promoting longevity.

The "effective dose" here indicated a usage amount that was enough to achieve the aforementioned effect of prevention and/or treatment. For the in vitro cell culture experiments, the aforementioned effective doses were defined as "µg/mL" in which "mL" was based on the total volume of the cell culture medium for each cell culture. For the animal model experiment, the aforementioned effective dose was defined as "g/60 kg body weight/day". Moreover, the amount of the effective dose obtained from the in vitro cell culture experiment can be converted into the effective dose for animal use via the following calculation:

I. General speaking (Reagan-Shaw et al., 2009), 1 "µg/mL" (the effective dose based on in vitro cell culture experiments) was equivalent to 1 "mg/kg body weight/day" (the effective dose according to animal model experiments). Moreover, the metabolizing rate of mice was six times higher than that of human.

II. Thus, if the effective dose according to an in vitro cell experiment was 500 µg/mL, the effective dose for mice shall be calculated as 500 mg/kg body/day (i.e., 0.5 g/kg body weight/day). Furthermore, based on the aforementioned differences of metabolize rate, the reasonable effective dose for a human shall be calculated as 5 g/60 kg body weight/day.

III. Referring to the aforementioned experience results, since the effective dose was 1.5 µg/mL according to the in vitro cell culture experiment, the effective dose for mice experiment was estimated as 1.5 mg/kg body weight/day, and the reasonable effective dose for a human usage should be 0.015 g/60 kg body weight/day.

In one preferred embodiment, the effective dose of the lactic acid bacteria having the active substances included in the composition was 10 mg/60 kg body weight/day.

The composition further includes an additive. In a preferred embodiment, the additive can be an excipient, a preservative, a diluent, filler, an absorbefacient, a sweetener, or any combination of the above. The excipient can be citric acid, calcium carbonate, tricalcium diphosphate, sucrose, or any combination of the above. The preservative can extend the shelf life of the composition, such as applying with benzyl alcohol and parabens. The diluent can be selected from a group consisting of water, ethyl alcohol, propylene glycol, glycerol, or any combination of the above. The filler can be selected from a group consisting of lactose, galactose, high molecular weight polyethylene glycol or any combination of the above. The absorbefacient can be dimethyl sulfoxide (DMSO), azone, propylene glycol, glycerol or any combination of the above. The sweetener can be Acesulfame K, aspartame, saccharin, sucralose, neotame or any combination of the above. Except for the additives listed above, other proper additives can be optionally selected under the premise that the medical effects of the compositions comprising the lactic acid bacteria having active substances are not affected.

The composition can be developed into different products in the medicinal field. In a preferred embodiment, the composition can be a drug, a feed, a drink, a nutritional supplement, a dairy product, a food for eldery people, a food for baby or health food.

The composition can be adapted to different forms based on the requirement of the subject. In a preferred embodiment, the form of the composition can be powder, a tablet, a pellet, a suppository, a microcapsule, an ampoule, a liquid or a spray.

The composition can be applied to animals or humans. Without affecting the function of the active substance of lactic acid bacteria, the composition comprising the lactic acid bacteria having the active substances can be made in any drug forms, and applied to animals or humans in a preferred way based on the drug form.

Preparation of Composition.

The following aspect of composition 1 was shown as an example if the composition comprising the lactic acid bacteria having the active substances was applied for food use.

Composition 1: The lyophilized powder of the lactic acid bacteria strain NO. I (GKK2) having the active substances (20 weight %, or wt. %) were mixed completely with the preservative benzyl alcohol (8 wt. %), diluent glycerol (7 wt. %) and pure water (65 wt. %) followed by 4° C. storage. The aforementioned wt. % denoted the weight ratio of each composite accounting in the total weight of the composition.

The following aspect of composition 2 was shown as an example if the composition comprising the lactic acid bacteria having the active substances was applied for medical use.

Composition 2: The lyophilized powder of the lactic acid bacteria strain NO. I (GKK2) having the active substances (20 wt. %) was mixed completely with the preservative benzyl alcohol (8 wt. %), diluent glycerol (7 wt. %), excipient sucrose (10 wt. %) and pure water (55 wt. %), followed by 4° C. storage. The aforementioned wt % denoted the weight ratio of each composite accounting in the total weight of the composition.

What is claimed is:

1. A method of promoting longevity by administering to a subject in need thereof a therapeutically effective amount of a composition comprising *Bifidobacterium lactis* having active substances, in which the *Bifidobacterium lactis* is deposited in Bioresource Collection and Research Center (BCRC), Food Industry Research and Development Institute, Hsinchu 30062, Taiwan, and China General Microbiological Culture Collection Center (CGMCC), Chinese Academy of Sciences, Beijing 100101, People's Republic of China, on Jan. 12, 2018 with an accession number of BCRC 910826 and CGMCC 15205, respectively.

2. The method of claim 1, wherein the composition enhances gene expression of Cisd2 of the subject.

3. The method of claim 1, wherein the composition decreases and/or delays mitochondrial damage of the subject.

4. The method of claim 1, wherein the composition decreases and/or delays aging-related symptoms comprising neurodegenerative diseases, sarcopenia, or the combination thereof of the subject.

5. The method of claim 1, wherein an effective dosage of the *Bifidobacterium lactis* is 0.015 g/60 kg body weight/day while being administered to a human subject.

6. The method of claim 1, wherein an effective dosage of the *Bifidobacterium lactis* is 1.5 mg/kg body weight/day while being administered to a mouse subject.

* * * * *